United States Patent
Pai et al.

(10) Patent No.: US 11,620,782 B2
(45) Date of Patent: Apr. 4, 2023

(54) METHODS AND SYSTEMS FOR DETERMINING HUMAN BODY MODEL PARAMETERS, HUMAN BODY MODELS BASED ON SUCH PARAMETERS AND SIMULATING HUMAN BODIES BASED ON SUCH BODY MODELS

(71) Applicant: Vital Mechanics Research Inc., Vancouver (CA)

(72) Inventors: Dinesh Kochikar Pai, Vancouver (CA); Austin Caulfield Rothwell, Vancouver (CA); Alistair Charles Wick, Surrey (GB); Pearson Andrew Wyder-Hodge, Burnaby (CA); Ye Fan, Vancouver (CA); Egor Larionov, Vancouver (CA); Darcy Alexander Harrison, Stonewall (CA)

(73) Assignee: Vital Mechanics Research Inc., Vancouver (CA)

( * ) Notice: Subject to any disclaimer, the term of this patent is extended or adjusted under 35 U.S.C. 154(b) by 158 days.

(21) Appl. No.: 17/146,380

(22) Filed: Jan. 11, 2021

(65) Prior Publication Data
US 2021/0241511 A1 Aug. 5, 2021

Related U.S. Application Data

(63) Continuation of application No. PCT/CA2019/050983, filed on Jul. 16, 2019.
(Continued)

(51) Int. Cl.
*G06T 13/40* (2011.01)
*G06T 7/262* (2017.01)
(Continued)

(52) U.S. Cl.
CPC .............. *G06T 13/40* (2013.01); *A61B 5/107* (2013.01); *G06T 7/254* (2017.01); *G06T 7/262* (2017.01);
(Continued)

(58) Field of Classification Search
CPC . A61B 8/485; A61B 5/0053; A61B 2034/105; A61B 2090/064; A61B 5/107;
(Continued)

(56) References Cited

U.S. PATENT DOCUMENTS

| | | | |
|---|---|---|---|
| 5,628,230 A | 5/1997 | Flam | |
| 2005/0085728 A1* | 4/2005 | Fukuda | G01N 29/227 600/449 |

(Continued)

OTHER PUBLICATIONS

Pai et al., "The Human Touch: Measuring Contact With Real Human Soft Tissues", ACM Transactions on Graphics, vol. 37, No. 4, Article 58., Aug. 2018.
(Continued)

*Primary Examiner* — Xiao M Wu
*Assistant Examiner* — Scott E Sonners
(74) *Attorney, Agent, or Firm* — Todd A. Rattray; Oyen Wiggs Green & Mutala LLP (57) ABSTRACT

A method that simulates a response of a target person to one or more simulation inputs comprises: contacting a body of a first test subject with a force-sensing probe; measuring a first force applied by the probe to the body of the first test subject; obtaining a first relative movement comprising a first movement of the probe relative to the body of the first test subject; determining one or more model parameters associated with the body of the first test subject based on the measured first force and the first relative movement; incorporating the one or more model parameters into a target model of at least a portion of a body of a target person; obtaining a simulation input for application to the target model; and simulating a response of the target person in response to the simulation input using the target model.

19 Claims, 3 Drawing Sheets

Related U.S. Application Data (60) Provisional application No. 62/698,911, filed on Jul. 16, 2018.

(51) Int. Cl.
    *G06T 7/254* (2017.01)
    *G09B 23/30* (2006.01)
    *A61B 5/107* (2006.01)

(52) U.S. Cl.
    CPC .... *G09B 23/30* (2013.01); *G06T 2207/10028* (2013.01); *G06T 2207/30196* (2013.01); *G06T 2207/30208* (2013.01)

(58) Field of Classification Search
    CPC ........ A61B 2034/102; A61B 2034/104; G06T 13/40; G06T 17/20; G06T 19/20; G06T 2219/2021; G06T 17/00; G06T 2207/20081; G06T 2207/20084; G06T 2207/30196; G06T 2210/16; G06T 7/50; G06T 13/20; G06T 15/00; G06T 2215/16
    See application file for complete search history.

(56) References Cited

U.S. PATENT DOCUMENTS

| | | | |
|---|---|---|---|
| 2008/0200843 A1* | 8/2008 | Williams | A61B 5/103 600/587 |
| 2010/0076563 A1* | 3/2010 | Otto | A61B 5/103 623/20.14 |
| 2016/0058519 A1* | 3/2016 | Herr | A61F 2/5044 600/587 |
| 2016/0140750 A1 | 5/2016 | Pai et al. | |
| 2016/0203630 A1 | 7/2016 | Pai et al. | |
| 2017/0156662 A1 | 6/2017 | Goodall et al. | |
| 2017/0287213 A1* | 10/2017 | Loper | G06T 13/40 |

OTHER PUBLICATIONS

Portnoy et al., "Real-Time Patient-Specific Finite Element Analysis of Internal Stresses n the Soft Tissues of a Residual Limb", Annals of Biomedical Engineering, vol. 35, No. 1, Jan. 2007 (C) 2006) pp. 120-135.

Petron et al., "Multi-Indenter Device for in Vivo Biomechanical Tissue Measurement", IEEE Transactions on Neural Systems and Rehabilitation Engineering, vol. 25, No. 5, May 2017, pp. 426-435.

Tonuk et al., "Nonlinear Elastic Material Property Estimation of Lower Extremity Residual Limb Tissues", IEEE Transactions on Neural Systems and Rehabilitation Engineering, vol. 11, No. 1, Mar. 2003, pp. 43-53.

Yeung et al., "A 3D Biomechanical Human Model for Numerical Simulation of Garment-Body Dynamic Mechanical nteractions During Wear", The Journal of The Textile Institute, ISSN: 0040-5000 (Print) 1754-2340 (Online) Journal homepage: https://www.tandfonline.com/loi/tjti20, 2004.

Nie et al., "Comparison of two scaling approaches for the development of biomechanical multi-body human models", Springer Science+Business Media Dordrecht 2016, pp. 297-316.

* cited by examiner

METHODS AND SYSTEMS FOR DETERMINING HUMAN BODY MODEL PARAMETERS, HUMAN BODY MODELS BASED ON SUCH PARAMETERS AND SIMULATING HUMAN BODIES BASED ON SUCH BODY MODELS

REFERENCE TO RELATED APPLICATIONS

This application is a continuation of Patent Cooperation Treaty Application No. PCT/CA2019/050983 filed 16 Jul. 2019, which in turn claims priority from U.S. application No. 62/698,911 filed 16 Jul. 2018. For the purposes of the United States, this application claims the benefit under 35 U.S.C. § 119 of application No. 62/698,911, filed 16 Jul. 2018. Patent Cooperation Treaty application No. PCT/CA2019/050983 and U.S. application No. 62/698,911 (including its Appendices A and B) are hereby incorporated herein in their entirety by reference for all purposes. U.S. application No. 62/698,911 is referred to hereinafter as the "Provisional Application".

TECHNICAL FIELD

This invention relates to modeling and/or simulating one or more portions of the human body. Particular embodiments comprise methods and systems for determining human body model parameters (e.g. by measurement), developing human body models based on such human body model parameters and simulating human bodies based on such human body models.

BACKGROUND

Simulating the human body is one of the greatest challenges in the apparel industry, computer graphics, and in a myriad fields of human endeavor ranging from ergonomics to medicine. Most human body models used in computer graphics are purely kinematic, and cannot simulate how the human body would react to internal and external forces.

There have been significant recent advances in physics-based models of the human body, but these have focused on the numerical methods required for simulating soft tissues; the constitutive properties of these tissues have been chosen almost arbitrarily. Even though simulations based on such models may be useful for producing physically plausible jiggles and bulges, their utility outside the entertainment industry has been limited.

By contrast, applications in product design, e-commerce, and medicine need trustworthy models, whose simulation-based predictions can be relied upon to make decisions. For example, before an individual purchases a tight-fitting pair of jeans or a sports bra online, a trustworthy simulation may be desirable to predict how well the garment fits the individual, taking into account how the individual's body may deform when the garment is worn. Such accurate and personalized human body simulations are out of reach today.

Despite intense research effort, the human body remains one of the most mysterious and complex objects known to science. Soft tissues are composites made of many different living materials whose composition can vary significantly over the body, across individuals, and even under voluntary control (e.g. by flexing a muscle). It is not currently possible to simply look up the mechanical properties of, for example, a shoulder and plug it into a model or into a simulation. Despite these difficulties, there is a desire to create models of the human body (or portions thereof) and to provide trustworthy simulations of the real behavior of the human body based on such human body models.

There has been significant progress in the last decade in measuring human body appearance and shape, thanks to advances in computer vision, 3D depth cameras and other optical scanning technologies. However, the spatial distribution of the mechanical properties desirable for use in contact simulation cannot be easily measured by existing techniques. The mechanical behavior of soft tissues is highly non-linear; it is difficult to extrapolate properties derived from, say, ultrasound elastography, to those that can represent soft tissue compression, due to contact of the soft tissue with a garment or a wearable device.

The foregoing examples of the related art and limitations related thereto are intended to be illustrative and not exclusive. Other limitations of the related art will become apparent to those of skill in the art upon a reading of the specification and a study of the drawings.

SUMMARY

One aspect of the invention provides a method for simulating a response of a target person to one or more simulation inputs. The method comprises: contacting a first location of a body of a first test subject with a probe tip mechanically connected to a force sensor; measuring a first force applied by the probe tip to the first location of the body of the first test subject with the force sensor; obtaining a first relative movement, the first relative movement comprising a first movement of the probe tip relative to the first location of the body of the first test subject; determining one or more model parameters associated with the first location of the body of the first test subject based on the measured first force and the first relative movement; incorporating the one or more model parameters into a target model of at least a portion of a body of a target person; obtaining a simulation input for application to the target model; and over a series of discrete time steps, simulating a response (e.g. movement) of the at least a portion of the body of the target person in response to the simulation input using the target model, wherein simulating the response comprises using the target model to generate, for each discrete time step, at least one of: a simulated shape of a surface of the portion of the body of the target person; and simulated stresses and strains internal to the portion of the body of the target person.

Another aspect of the invention provides a method for simulating a response of a target person to one or more simulation inputs. The method comprises: contacting a first location of a body of a test subject with a probe tip mechanically connected to a force sensor; measuring a first force applied by the probe tip to the first location of the body of the test subject with the force sensor; measuring a first movement of the probe tip; measuring a first movement of the test subject; contacting a second location of the body of the test subject with the probe tip, the second location of the body of the test subject spaced apart from the first location of the body of the test subject; measuring a second force applied to the probe tip by the second location of the body of the test subject with the force sensor; measuring a second movement of the probe tip; measuring a second movement of the test subject; and determining one or more model parameters associated with the first and second locations of the body of the first test subject based on the first force, the second force, the first movement of the probe tip, the second movement of the probe tip, the first movement of the test subject and the second movement of the test subject; incorporating the one or more model parameters into a target model of at least a portion of a body of a target person; obtaining a simulation input for application to the target model; and over a series of discrete time steps, simulating a response (e.g. movement) of the at least a portion of the body of the target person in response to the simulation input using the target model, wherein simulating the response comprises using the target model to generate, for each discrete time step, at least one of: a simulated shape of a surface of the portion of the body of the target person; and simulated stresses and strains internal to the portion of the body of the target person.

Another aspect of the invention provides a method for simulating a response of a target person to one or more simulation inputs, the method comprising: contacting a first location of a body of a first test subject with a probe tip mechanically connected to a force sensor; measuring a first force applied to the probe tip by the first location of the body of the first test subject with the force sensor; obtaining a first relative movement, the first relative movement comprising a first movement of the probe tip relative to the first location of the body of the first test subject; contacting a second location of a body of a second test subject with the probe tip; measuring a second force applied by the probe tip to the second location of the body of the second test subject with the force sensor; obtaining a second relative movement, the second relative movement comprising a first movement of the probe tip relative to the second location of the body of the second test subject; and determining one or more model parameters of a target model associated with at least a portion of a body of a target person based on the first force and the first relative movement and the second force and the second relative movement; obtaining a simulation input for application to the target model; and over a series of discrete time steps, simulating a response (e.g. movement) of the at least a portion of the body of the target person in response to the simulation input using the target model, wherein simulating the response comprises using the target model to generate, for each discrete time step, at least one of: a simulated shape of a surface of the portion of the body of the target person; and simulated stresses and strains internal to the portion of the body of the target person.

Another aspect of the invention provides a method for simulating a response of a target person to one or more simulation inputs, the method comprising: contacting a first location of a body of a first test subject with a probe tip mechanically connected to a force sensor; measuring a first force applied to the probe tip by the first location of the body of the first test subject with the force sensor; obtaining a first relative movement, the first relative movement comprising a first movement of the probe tip relative to the first location of the body of the first test subject; obtaining supplementary first test subject data for the first test subject; contacting a second location of a body of a second test subject with the probe tip; measuring a second force applied by the probe tip to the second location of the body of the second test subject with the force sensor; obtaining a second relative movement, the second relative movement comprising a second movement of the probe tip relative to the second location of the body of the second test subject; obtaining supplementary second test subject data for the second subject; receiving one or more characteristics of a target person; comparing the one or more characteristics of the target person to the supplementary first test subject data and the supplementary second test subject data to choose one of (a) the first force and the first relative movement and (b) the second force and the second relative movement; determining one or more target model parameters associated with a target model associated with a portion of a body of the target person based the chosen one of (a) the first force and the first relative movement and (b) the second force and the second relative movement; obtaining a simulation input for application to the target model; and over a series of discrete time steps, simulating a response (e.g. movement) of the at least a portion of the body of the target person in response to the simulation input using the target model, wherein simulating the response comprises using the target model to generate, for each discrete time step, at least one of: a simulated shape of a surface of the portion of the body of the target person; and simulated stresses and strains internal to the portion of the body of the target person.

Obtaining the first relative movement may comprise: measuring a first movement of the probe tip; measuring a first movement of the first test subject at the first location; and accommodating for the measured first movement of the first test subject within the measured first movement of the probe tip (e.g. by subtracting, or otherwise removing the effect of, the measured first movement of the first test subject from the measured first movement of the probe tip) to obtain the first relative movement.

The simulation input may comprise one or more boundary conditions, which may be constant or which may vary over time. The simulation input may comprise a force input which may be constant or which may vary over time and which is applied to the at least a portion of the body of the target person. The simulation input may be based on a model of a garment (e.g. forces or energies associated with deformation of the garment when the garment contacts the portion of the body of the target).

The probe tip may apply force to the first location in six degrees of freedom (three rotational and three translational). The method may comprise measuring the force applied by the probe tip to the first test subject with the force sensor in six degrees of freedom. The method may comprise measuring movement of the probe tip with six degrees of freedom. The method may comprise measuring movement of the first test subject with six degrees of freedom.

The method may comprise obtaining supplementary test subject data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the test subject.

Measuring the first movement of the probe tip may comprise tracking one or more markers on the probe. Measuring the first movement of the probe tip comprises optically tracking one or more markers on the probe. Measuring the first movement of the first test subject may comprise tracking one or more markers on the first test subject. Measuring the first movement of the first test subject may comprise optically tracking one or more markers on the first test subject.

Accommodating for the measured first movement of the first test subject within the measured first movement of the probe tip to obtain the first relative movement may comprise inverting a transformation matrix of the first test subject relative to a world coordinate system, and multiplying the inverted transformation matrix on the right hand side by a transformation matrix of the probe relative to the world coordinate system to produce a transformation matrix of the probe relative to the body.

The one or more model parameters may comprise one or more of: elasticity, mass density, skin friction, reference body shape, and effective skin thickness of the first test subject. The one or more model parameters comprise one or more sliding thick skin model parameters (e.g. of the sliding thick skin model described in Appendix B of the Provisional Application).

Determining the one or more model parameters associated with the first location of the first test subject based on the measured first force and the first relative movement may comprise: (a) computing results of a calibration simulation, over a set of discrete time points for which the measured first force and corresponding first relative movement are known, the calibration simulation using a current set of model parameters and taking as input one of: the measured first force and corresponding first relative movement; (b) adjusting the current set of model parameters; and (c) repeating steps (a) and (b) to iteratively minimize a residual error, which compares the results of a current calibration simulation to the other one of: the measured first force and the first relative movement, to thereby equate the one or more model parameters with the current set of model parameters when the residual error is below a threshold.

Determining the one or more model parameters associated with the first location of the first test subject based on the measured first force and the first relative movement may comprise: (a) computing results of a calibration simulation, over a set of discrete time points for which the measured first force and corresponding first relative movement are known, the calibration simulation using a current set of model parameters and taking as input one of: the measured first force and corresponding first relative movement; (b) adjusting the current set of model parameters; and (c) repeating steps (a) and (b) to iteratively minimize a residual error, which compares the results of a current calibration simulation to the other one of: the measured first force and the first relative movement, to thereby equate the one or more model parameters with the current set of model parameters when the residual error is below a threshold.

Determining the one or more model parameters associated with the first location of the first test subject based on the measured first force and the first relative movement may comprise: (a) computing results of a calibration simulation, over a set of discrete time points for which the measured first force and corresponding first relative movement are known, the calibration simulation using a current set of model parameters and taking as input one of: the measured first force and corresponding first relative movement; (b) adjusting the current set of model parameters; and (c) repeating steps (a) and (b) to iteratively minimize a residual error, which compares the results of a current calibration simulation to the other one of: the measured first force and the first relative movement, to thereby equate the one or more model parameters with the current set of model parameters when the residual error is below a threshold.

Determining the one or more model parameters associated with the first location of the first test subject based on the measured first force and the first relative movement may comprise a curve fitting process (e.g. wherein the curve fitting process varies the one or more model parameters so that, given the first relative movement, a model incorporating the one or more model parameters predicts the first force).

The method may comprise: contacting a second location of the body of the first test subject with the probe tip, the second location of the first test subject spaced apart from the first location of the first test subject; measuring a second force applied by the probe tip to the second location of the body of the first test subject with the force sensor; obtaining a second relative movement, the second relative movement comprising a second movement of the probe tip relative to the second location of the body of the first test subject; determining one or more second model parameters associated with the second location of the body of the first test subject based on the measured second force and the second relative movement; and incorporating the one or more second model parameters into the target model.

Obtaining the second relative movement may comprise: measuring a second movement of the probe tip; measuring a second movement of the first test subject at the second location; and accommodating for the measured second movement of the first test subject within the measured second movement of the probe tip (e.g. by subtracting, or otherwise removing the effect of, the measured second movement of the first test subject from the measured second movement of the probe tip) to obtain the second relative movement.

The method may comprise creating a first test subject model comprising: the one or more model parameters associated with the first location of the body of the first test subject and the one or more second model parameters associated with the second location of the body of the first test subject; wherein incorporating the one or more model parameters into the target model of the at least a portion of the body of the target person and incorporating the one or more second model parameters into the target model may comprise basing the target model at least in part on the first subject model (e.g. including both the one or more model parameters associated with the first location of the body of the first test subject and the one or more second model parameters associated with the second location of the body of the first test subject).

Creating the first test subject model may comprise: for each of one or more other locations of the body of the first test subject spaced apart from the first location and from the second location, determining one or more model parameters associated with the other location of the body of the first test subject based on (e.g. interpolation between): the one or more model parameters and the one or more second model parameters; or based on: the first force, the second force, the first relative movement and the second relative movement.

The method may comprise: contacting a third location of a body of a second test subject with a probe tip mechanically connected to a force sensor; measuring a third force applied by the probe tip to the third location of the body of the second test subject with the force sensor; obtaining a third relative movement, the third relative movement comprising a third movement of the probe tip relative to the third location of the body of the second test subject; determining one or more third model parameters associated with the third location of the body of the second test subject based on the measured third force and the third relative movement; and incorporating the one or more third model parameters into the target model.

Obtaining the third relative movement may comprise: measuring a third movement of the probe tip; measuring a third movement of the second test subject at the third location; and accommodating for the measured third movement of the second test subject within the measured third movement of the probe tip (e.g. by subtracting, or otherwise removing the effect of, the measured third movement of the second test subject from the measured third movement of the probe tip) to obtain the third relative movement.

The method may comprise: creating a first test subject model comprising: the one or more model parameters associated with the first location of the body of the first test subject; creating a second test subject model comprising: the one or more third model parameters associated with the third location of the body of the second test subject; and wherein incorporating the one or more model parameters into the target model of the at least a portion of the body of the target person and incorporating the one or more third model parameters into the target model comprise basing the target model on a weighted combination of the first test subject model and the second test subject model.

The method may comprise: for each of the first subject and the second subject, obtaining supplementary test subject data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the first or second test subject; for the target person, obtaining supplementary target person data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the target person; wherein the weighted combination of the first test subject model and the second test subject model is based at least in part on a comparison of the target person supplementary data with the first test subject supplementary data and a comparison of the target person supplementary data with the second test subject supplementary data.

The method may comprise: contacting a third location of a body of a second test subject with a probe tip mechanically connected to a force sensor; measuring a third force applied by the probe tip to the third location of the body of the second test subject with the force sensor; obtaining a third relative movement, the third relative movement comprising a third movement of the probe tip relative to the third location of the body of the second test subject; determining one or more third model parameters associated with the third location of the body of the second test subject based on the measured third force and the third relative movement; constructing a population model, the population model comprising the one or more model parameters associated with the first location of the body of the first test subject and the one or more third model parameters associated with the third location of the body of the second test subject; and constructing the target model based on the population model.

Constructing the target model based on the population model may comprise constructing the target model based on a weighted combination of the one or more model parameters associated with the first location of the body of the first test subject and the one or more third model parameters associated with the third location of the body of the second test subject.

The method may comprise: for each of the first subject and the second subject, obtaining supplementary test subject data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the first or second test subject; for the target person, obtaining supplementary target person data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the target person; wherein the weighted combination of the one or more model parameters associated with the first location of the body of the first test subject and the one or more third model parameters associated with the third location of the body of the second test subject is based at least in part on a comparison of the target person supplementary data with the first test subject supplementary data and a comparison of the target person supplementary data with the second test subject supplementary data.

Constructing the target model based on the population model may comprise generating the target model based on a statistical abstraction of the population model. The method may comprise: for each of the first subject and the second subject, obtaining supplementary test subject data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the first or second test subject; for the target person, obtaining supplementary target person data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the target person; and wherein the statistical abstraction of the population model is based at least in part on a comparison of the target person supplementary data with the first test subject supplementary data and a comparison of the target person supplementary data with the second test subject supplementary data.

Simulating the response of the at least a portion of the body of the target person may comprise simulating an interaction of the target model with a clothing model, the clothing model and/or the target model comprising any of the features, combinations of features or sub-combinations of features described in Appendix B of the Provisional Application.

Simulating the response may comprise evaluating (e.g. quantifying) a fit of the garment on the body of the target person. Simulating the response may comprise displaying a simulation result, the displayed simulation result showing the fit of the garment on the body of the target person.

The target person may be different than any of the test subjects. The target person may be the first test subject.

The method may comprise: accommodating for the measured first movement of the test subject within the measured first movement of the probe tip (e.g. by subtracting, or otherwise removing the effect of, the measured first movement of the test subject from the measured first movement of the probe tip) to obtain a first relative movement;

accommodating for the measured second movement of the test subject within the measured second movement of the probe tip (e.g. by subtracting, or otherwise removing the effect of, the measured second movement of the test subject from the measured second movement of the probe tip) to obtain a second relative movement wherein determining one or more model parameters associated with the first and second locations of the body of the first test subject is based on the first and second forces and the corresponding first and second relative movements.

Determining one or more model parameters of the target model may comprise: creating a first test subject model comprising one or more model parameters associated with the first location of the body of the first test subject based on the first force and the first relative movement; creating a second test subject model comprising one or more model parameters associated with the second location of the body of the second test subject based on the second force and the second relative movement; and basing one or more model parameters of the target model on a weighted combination of the first test subject model and the second test subject model.

The method may comprise: for each of the first subject and the second subject, obtaining supplementary test subject data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the first or second test subject; for the target person, obtaining supplementary target person data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the target person; wherein the weighted combination of the first test subject model and the second test subject model is based at least in part on a comparison of the target person supplementary data with the first test subject supplementary data and a comparison of the target person supplementary data with the second test subject supplementary data.

Determining one or more model parameters of the target model may comprise: constructing a population model, the population model based on: a first test subject model comprising one or more model parameters associated with the first location of the body of the first test subject based on the first force and the first relative movement and a second test subject model comprising one or more model parameters associated with the second location of the body of the second test subject based on the second force and the second relative movement; and constructing the target model based on the population model.

Constructing the target model based on the population model may comprise constructing the target model based on a weighted combination of the one or more model parameters associated with the first location of the body of the first test subject and the one or more second model parameters associated with the second location of the body of the second test subject.

The method may comprise: or each of the first subject and the second subject, obtaining supplementary test subject data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the first or second test subject; for the target person, obtaining supplementary target person data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the target person; wherein the weighted combination of the one or more model parameters associated with the first location of the body of the first test subject and the one or more second model parameters associated with the second location of the body of the second test subject is based at least in part on a comparison of the target person supplementary data with the first test subject supplementary data and a comparison of the target person supplementary data with the second test subject supplementary data.

Constructing the target model based on the population model may comprise generating the target model based on a statistical abstraction of the population model.

The method may comprise: for each of the first subject and the second subject, obtaining supplementary test subject data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the first or second test subject; for the target person, obtaining supplementary target person data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the target person; wherein the statistical abstraction of the population model is based at least in part on a comparison of the target person supplementary data with the first test subject supplementary data and a comparison of the target person supplementary data with the second test subject supplementary data.

Determining the one or more model parameters associated with the first location of the target person may comprise: mapping the first location of the first test subject to a first location on a target person; and mapping the second location of the second test subject to the first location on the target person.

Mapping the first location of the first test subject to the first location on the target person may be based at least in part on supplementary test subject data comprising one or more of: body shape, a three-dimensional body scan, body weight, body height, body mass index, locations of anatomical landmarks, anthropometric measurements, ethnicity, Fitzpatrick skin type, clothing size, and exercise preferences.

Mapping the second location of the second test subject to the first location on the target person may be based at least in part on supplementary test subject data comprising one or more of: body shape, a three-dimensional body scan, body weight, body height, body mass index, locations of anatomical landmarks, anthropometric measurements, ethnicity, Fitzpatrick skin type, clothing size, and exercise preferences.

Mapping the first location of the first test subject to the first location on the target person may comprise mapping an anatomical landmark of the first test subject to an anatomical landmark of the target person.

Mapping the second location of the second test subject to the first location on the target person may comprise mapping an anatomical landmark of the second test subject to an anatomical landmark of the target person.

Each of the supplementary first test subject data and the supplementary second test subject data may comprise one or more of: body shape, a three-dimensional body scan, body weight, body height, body mass index, locations of anatomical landmarks, anthropometric measurements, ethnicity, Fitzpatrick skin type, clothing size, and exercise preferences.

Further aspects and example embodiments are illustrated in the accompanying drawings and/or described in the following description.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

One aspect of the invention provides methods and systems for modeling and/or simulating one or more portions of the human body. Particular embodiments comprise methods and systems for determining human body model parameters (e.g. by measurement of the response of one or more human test subjects to contact-based probing to obtain response parameters), developing human body models based on such human body model parameters and simulating human bodies based on such human body models.

Figure 1:
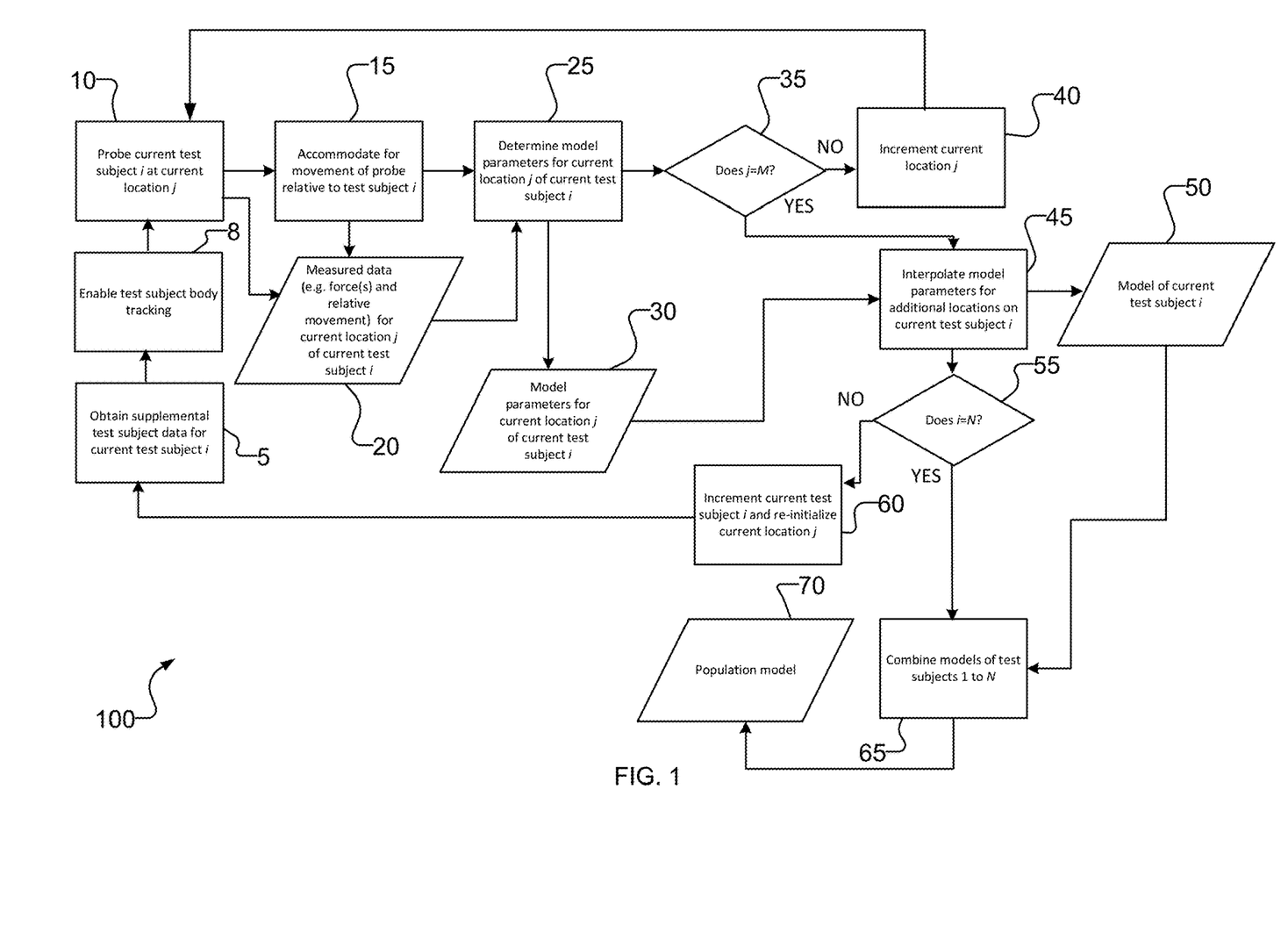
FIG. 1 is a block diagram of a method for obtaining human body model parameters (e.g. response parameters of actual human subjects to contact-based probing) and for generating human body models based at least in part on such human body model parameters according to one embodiment of the invention.

FIG. 1 is a block diagram of a method 100 for obtaining human body model parameters (e.g. which may be based on the responses of one or more actual human test subjects to contact-based probing) and for generating a human body model based at least in part on such human body model parameters according to one embodiment of the invention. The method 100 process of obtaining human body model parameters involves measuring the responses (or response parameters) of one or more actual human test subjects to contact based probing. In this description and in Appendix A of the Provisional Application, human test subjects may be referred to as participants. Such measurement of test subject response parameters may be implemented for a number of body locations, M, for each of a number, N, of test subjects. Each test subject may be represented by a test subject index, i, and each body location of a test subject, i, may be represented by a location index, j.

Method 100 starts at block 5 where supplementary test subject data, such as body shape, 3D scans, 3D scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like are obtained for a first test subject (e.g. i=1).

The block 5 supplementary test subject data may be obtained by any one or more of a plurality of methods ranging from questionnaires to measurement of the current test subject using imaging devices. Skin type may be recorded using Fitzpatrick skin type questionnaire, or may be measured using instruments that record erythema, melanin, and/or other content of skin. Three dimensional body scans representative of body shape may be acquired, for example, by any of a plurality of imaging methods, including, without limitation, depth cameras, laser scanners, MRI, CT, as well as regular cameras combined with computer vision and/or artificial intelligence methods. Imaging devices used in block 5 to obtain supplementary test subject data may be part of a smart phone (e.g. Apple iPhone™, Android™ phone), a smart home device (e.g. Amazon Echo Look™, Google Home™), a laptop (e.g. using Intel RealSense™ technology), or a gaming device (e.g., Microsoft Kinect™). 3D scans may be acquired without garments on the body, or with one or more garments on the body. Such garments may be normal garments or specially constructed calibration garments with known material properties.

The block 5 supplementary test subject data may subsequently be used to relate a target person's supplementary data to construct a personalized model of the target person, where the model is used to construct a personalized simulation of the target person as discussed further herein.

Prior to probing test subject i in block 10 for the first time, method 100 may optionally involve enabling tracking of the body of the $i^{th}$ test subject in block 8. In block 8, markers may be identified on the body of test subject i for subsequent tracking of the test subject's body motion. Such markers may include natural markers, such as visible patterns on the skin (e.g. skin color patterns, geometric patterns due to bony landmarks and/or the like). Markers may additionally or alternatively include objects (e.g. tape, retroreflective markers and/or the like) applied to the body of the test subject to permit tracking of the marker locations using a motion capture system (e.g. Vicon™).

Method 100 then proceeds to block 10, where the current test subject, i, is probed at a first body location j=1. In a first iteration of block 10, the current test subject, i, is probed at a first location, j=1. In some embodiments, at block 10 the current test subject, i, is probed multiple times at the first location, j=1, (or sufficiently close to the same location to be considered, for the purposes of the present disclosure, at the same location). The body of the test subject is probed using an instrumented device (see Appendix A of the Provisional Application which describes a probe device that may be used for this purpose). The probe device makes contact with the surface of the body of the test subject at a small region which may be referred to as the "contact patch" and records data obtained for each contact. The probe may be hand-held. The probe may comprise a separate device or may comprise an add-on to a hand-held, laptop or desktop computer, mobile device, or smart phone. The probe may be communicatively connectable to such computing device(s).

Forces and/or torques (henceforth referred to herein as "forces" for brevity) applied by the probe tip to the contact patch over time may be recorded as part of block 10 and are shown in FIG. 1 as part of measured data 20. In some embodiments, measured force data 20 may be recorded using a force/torque sensor connected to the probe tip. Force data 20 may additionally or alternatively be measured using strain gauges embedded in the probe tip. Force data 20 may additionally or alternatively be measured optically by recording the motion of a calibrated flexure in the probe tip. Force data 20 may be measured at a different location connected to the probe tip and subsequently transformed to the probe tip.

The movement of the probe tip is also measured and recorded as part of block 10 and are shown in FIG. 1 as part of measured data 20.

In some embodiments, measured data 20 may be obtained by measuring the movement of the probe tip with respect to a world coordinate system, attached to the world. The measured movement data 20 may be measured by any suitable method, such as, by way of non-limiting example, by tracking the movement of markers attached to the probe that are tracked using a motion capture system; by using inertial sensors embedded in the probe; by using magnetic sensors; by using cameras embedded in the probe that can track the movement of features of the external world; and/or the like. The movement of the test subject's body may also be measured at the same time with respect to the world coordinate system by any suitable method. Such test subject body movement may also be recorded as part of measured data 20. Such test subject body movement may be used (in block 15 of the illustrated embodiment) to determine the relative movement of the probe tip relative to the test subject body (e.g. by subtracting or otherwise removing the test subject body movement from the probe tip movement). This block 15 method of removing the measured body movement from the measured probe tip movement to obtain the relative probe tip movement may be referred to as accommodating for the movement the test subject body within the measured probe tip movement to obtain the relative probe tip movement. Such block 15 relative movement may also be recorded as part of measured data 20 (FIG. 1). As in all cases, the body movement of the test subject may be measured at a different location connected to the probe tip and subsequently transformed to the probe tip.

In some embodiments, movement of the probe tip is measured (e.g. in block 10 and/or in block 15) with respect to other parts of the body (which may be referred to as "anchor points") at a distance from the contact patch to directly measure the relative movement of the probe tip relative to the body. Relative movement measured or otherwise determined in this manner may be recorded as part of measured data 20. Such relative movement may be measured by mechanically connecting a part of the probe to the anchor points and measuring the position of the probe tip relative to the anchor points. Such relative movement may additionally or alternatively be measured optically by imaging the anchor points from on board cameras in the probe.

In some embodiments, deformation of the outer surface (e.g. the skin) of the test subject's body in the vicinity of the contact patch may be measured by a suitable imaging system (e.g. as a part of block 10). In some such embodiments, the imaging system that performs this function may be integrated with the probe device (see Appendix A of the Provisional Application, section 3, FIGS. 2 and 3) and may be referred to as an onboard imaging system for this reason. The onboard imaging system may include a depth sensor or may comprise one or more image sensing apparatus. Such image sensing apparatus may be positioned to provide complete coverage of skin movement in the vicinity of the contact patch. The motion of the skin may then be estimated from a sequence of images using any suitable method (e.g. optical flow; 3D range flow; digital image correlation; feature tracking; and/or the like). The movement of the skin in the vicinity of the contact patch may also be recorded as part of measured data 20.

For each location j, a plurality of probing operations (e.g. movements which cause the probe to contact the body of the test subject) may be performed to achieve various deformations of the test subject's body and highlight the anisotropic properties of the test subject's underlying tissue. One type of probing operation (e.g. movement) may be in a direction generally aligned with a normal vector of the test subject's skin surface. Another type of probing operation (e.g. movement) may be a side-to-side movement that is generally tangential to the test subject's skin surface. Another type of probing operation (e.g. movement) may involve twisting the probe around an axis that is generally normal (e.g. +/−) 10° to the contact patch. The probe tip may maintain contact with the skin throughout any such probing operations. In some probing operations, the probe tip is prevented from slipping on the skin. In some embodiments, adhesives may be placed on the probe tip to reduce slippage or materials having relatively high coefficients of sliding friction may be used on the surface of the probe tip. In some probing operations, the probe tip is permitted to slide on the skin of the test subject to permit subsequent estimation of skin friction properties.

Block 15 is now described in more detail. As discussed above in some embodiments, block 15 is combined with block 10 or is inherent in the block 10 process. Block 15 involves determining relative movement of the probe tip relative to the current body test subject, i. This may be referred to as accommodating for the measured motion of the body of the test subject within the measured probe tip movement to obtain the relative probe tip movement. Obtaining the relative probe tip movement in block 15 or otherwise can be desirable for subsequent determinations of the parameters of a body contact model (as discussed further below in connection with block 25). If the movement of the probe was measured relative to the same world coordinate system as the movement of the test subject's body, then the movement of the probe tip relative to the body may be determined (in block 15) at each time step by: inverting the transformation matrix of the body relative to the world coordinate system, and multiplying the inverted transformation matrix of the body relative to the world on the right hand side by the transformation matrix of the probe relative to the world to produce a transformation matrix of the probe relative to the body.

As discussed above, the relative movement of the probe tip determined in block 15 may be recorded as part of measured data 20. Measured data 20 may comprise one or more force values and the relative movement for current location, j, of current test subject, i. The force values summarize the forces applied to the contact patch during the various probing operations and may include the three dimensional force and three dimensional torque applied on the body of the test subject by the probe tip.

Method 100 continues at block 25, where measured data 20 is received as input to determine human body model parameters for the current location, j, of current test subject, i. Block 25 may output model parameter data 30, which may comprise the model parameters for current location, j, of current test subject, i.

Model parameters 30 comprise parameters of a human body model that may be used in a computer-implemented simulation of a human body or portion thereof. A non-limiting example of a computer-implemented simulation of a human body is a finite element simulation of the elastic deformation of the body due to contact with a tight fitting garment. Such a finite element simulation may be based on a model that includes model parameters that represent elasticity, skin thickness, mass density, skin friction, and/or the like. These model parameters may be dependent on a location on the body and may vary continuously over the surface of the body. These model parameters may be received as inputs to the model. Such a finite element model may also comprise a parameter or set of parameters that represent a rest or reference body shape. This rest or reference body shape, which may be received as an input to the model, may be different from the body shape that is scanned (e.g. in blocks 8, 10, 15 and/or 25) due to, for example, forces due to gravity acting on the test subject and/or clothing worn by the test subject which interacts with the test subject's body. A human body model for such a computer-implemented simulation of a human body may comprise data representing the reference shape of the body and the distribution of the parameters over a surface of the reference shape.

Model parameters 30 may include constitutive properties (e.g. elasticity parameters) of the body tissues of test subject i that are probed and, in some embodiments, other properties of the tissue of test subject i, such as mass density, effective thickness and/or the like. Non-limiting examples of elasticity parameters include the parameters of non-linear hyperelastic models, such as the Mooney-Rivlin model, Gasser-Ogden-Holzapfel model, polynomial hyperelastic models, related models and/or the like. Such constitutive models may account for the anisotropic behavior of tissue deformation in different material directions and may include orthotropic models.

Model parameters 30 may also or alternatively include dissipation parameters representative of hysteresis properties of human tissues such as, for example, viscosity, coefficient of internal friction, and parameters of Ogden-Roxburgh and Safadi-Rubin pseudo-elasticity models.

Model parameters 30 may also or alternatively include surface friction parameters. Non-limiting examples of surface friction parameters include the coefficient of a Coulomb friction model, and parameters of an adhesion friction model.

Model parameters 30 determined in block 25 may include the effective thickness of the soft tissue layer at the surface of the body of the current test subject, i. Note that effective thickness may not correspond to an actual thickness of a part of the body; rather, it may comprise a thickness that, when used with a corresponding constitutive property, approximates the deformation behavior of the skin of the test subject's body at the surface. Model parameters 30 may vary over different locations j on the surface of the body of any individual test subject.

One non-limiting example of model parameters 30 comprise the set of parameters for the sliding thick skin (STS) model described in Appendix A of the Provisional Application, Section 5 and/or Appendix B of the Provisional Application. In this example, the model parameters 30 are estimated in block 25 by performing a model calibration simulation, which may simulate a simulation input applied to a small "skin puck" at the contact location, j. In some embodiments, model parameters 30 may be estimated in block 25 by performing a model calibration simulation of a larger body segment or the full body.

Another set of model parameters 30 that may be determined in block 25 in some embodiments comprise the parameters of a machine learning model. Such a machine learning model may be considered a black-box with a number of parameters that may be learned from measured data 20. Non-limiting examples of such model parameters 30 include weights and number of layers of a deep neural network.

Model parameters 30 may be estimated at block 25 from the force and relative movement data that form part of measured data 20. In some embodiments, block 25 may additionally receive as input a population model 70 obtained from measurements of other test subjects or from other measurements of the same test subject as a Bayesian prior probability distribution in estimating model parameters 30.

In one approach, the model parameters at each contact location may be estimated in block 25 by comparing the results of performing a computer-implemented model-calibration simulation using an initial set of model parameters (e.g. using movements or forces similar to those which were probed in block 10 and recorded in measured data 20) and comparing the model-calibration simulation results to the measured data 20 to compute a residual error. The initial set of model parameters may then be adjusted (e.g. by a suitable optimization algorithm and/or the like) to search for a set of model parameters that reduce the residual error to an acceptable range. This model-calibration simulation process may be iterative in the sense that the initial set of model parameters may be iteratively adjusted to arrive at final model parameters 30. As a part of block 25, some model parameters may be fitted directly to measured data 20 by a curve fitting or averaging. As part of block 25 the rest or reference shape of the body may be estimated from a 3D scan with or without a calibration garment worn.

One non-limiting example embodiment of model parameter estimation involving a model-calibration simulation is described in Appendix A of the Provisional Application, Section 5.2, in which the behavior of a 3D finite-element model-calibration simulation is performed to fit the model behavior to the measured force, probe tip movement and surface deformation measured using optical flow. In accordance with this technique, by minimizing the difference between model-calibration simulated force and force recorded in block 10 as a part of measured data 20, and between simulated optical flow and optical flow recorded in block 10 as part of measured data 20, the material properties of the tissue may be estimated and the model parameters 30 may be obtained. In this non-limiting example, model parameters 30 may be estimated at block 25 by performing a model calibration simulation of a small "skin puck" at the contact location j. In some embodiments, model parameters 30 may additionally or alternatively be estimated in block 25 by performing a model calibration simulation of a larger body segment or the full body.

Method 100 then proceeds to block 35. At block 35, if current location index, j, is not equal to (e.g. less than) the number of locations, M, to be probed on the current test subject, i, then method 100 increments the location index j (in block 40) and returns to block 10, where method 100 repeats blocks 10, 15, 25, 35 with the incremented current location index, j and a corresponding different location on the body of the current test subject, i. At block 35, if current location index, j, is equal to the number of locations M to be probed on current person, i, then method 100 continues to block 45.

Block 45 may receive model parameters 30 as input. Based at least in part on model parameters 30, block 45 may comprise determined model parameters for additional locations (e.g. other locations that were expressly probed in block 10) on current test subject, i. The block 45 process may comprise interpolation between the model parameters associated with expressly probed locations. Block 45 may output a body model corresponding to the body of the current test subject, i. Model parameters 30 may comprise data measured at discrete (e.g. expressly probed) locations over the surface of the body of the $i^{th}$ test subject. In block 45 the model parameters at these discrete locations may be interpolated to provide estimates of the model parameters at intervening locations (e.g. locations that were not expressly probed) to produce a set of model parameter values having a finer discretization over the surface of the body of the $i^{th}$ test subject. The block 45 interpolation may be performed by any suitable method for scattered data interpolation (non-limiting examples of such interpolation techniques include kernel density estimation, polynomial interpolation, subdivision methods and/or the like).

Method 100 continues at block 55. At block 55, if current person index, i, is not equal to (e.g. less than) the number of persons, N, to be probed, then method 100 increments the test subject index i (i.e. selects a new test subject) in block 60 and then returns to block 5, where method 100 repeats blocks 5, 8, 10, 15, 25, 35, 40, 45, 55 with the incremented test subject index, (and the corresponding new test subject). At block 55, if current test subject index, i, is equal to the number of test subjects, N, to be probed in method 100, then method 100 continues to block 65. In some embodiments, where it is desired to obtain a model of only a single person (e.g. N is equal to one), method 100 may stop at block 45 or method 100 may skip from block 45 to block 78 where one or more simulations are performed using model 50 corresponding to the single subject. Such block 78 simulations may comprise simulations of clothing garments and the interaction of such garments with model 50, as discussed further herein.

Once probing has been completed for the N desired test subjects (block 55 YES branch), method 100 proceeds to block 65. Block 65 may comprise combining the models 50 outputted at block 45 for each test subject from 1 to N. Block 65 may output a population model 70 based at least in part on the individual models 50 output at block 45 for each test subject from 1 to N. In some embodiments, there is only a single person (e.g. N is equal to one) and nothing occurs at block 65 (e.g. the population model 70 may be considered to be the individual test subject model 50 for the individual test subject Where N is greater than one, combining the various individual test subject models 50 to obtain population model 70 in block 65 may comprise combining different individual test subject models 50 after representing them on a common reference human body shape.

Population model 70 may include one or more human body "templates" that represent normative human body shape(s). There may be different templates for different clusters of humans sharing characteristics, such as, by way of non-limiting example, biological sex, age, height, weight, body mass index and/or the like. Each template body may include data on anatomical landmarks and a body surface. Each template may include one or more additional data to facilitate simulation, such as, by way of non-limiting example, an animation rig, a finite element mesh and/or the like.

An invertible mapping, $\Phi$, that registers the human body template to the body of each test subject may then be constructed using the supplemental test data obtained in block 5, including, for example, anatomical landmarks, 3D scans, body shape, other anthropometric data and/or the like. The mapping $\Phi$ may be constructed as a mapping that aligns each template anatomical landmark, $a_t$, after applying the mapping to produce $\Phi(a_t)$ as closely as possible with the test subject's corresponding anatomical landmark $a_s$, and also aligns the mapped body surface $\Phi(S_t)$ to the body surface of the test subject $S_s$. Any suitable method to minimize the error between the anatomical landmarks and body shapes may be used. Examples include minimizing a weighted norm of the alignment error, such as the 2-norm, 1-norm, or infinity norm. Any suitable regularization method may be used to make the registration well-posed. Regularization methods may include imposing a degree of smoothness to the $\Phi$ mapping. Different templates may be registered to each other by a similar process of aligning anatomical landmarks and body shapes, thereby permitting all body models to be registered.

Since $\Phi$ is invertible, the model parameters 50 of an individual test subject's body may be pulled back from their locations on the subject's body to corresponding locations on the template body by utilizing the inverse map $(\Phi)^{-1}$. Thus, a plurality of test subjects' individual model parameters 50 may be represented over the surface of a template body, and may be compared and combined to produce population model 70.

In one embodiment, perhaps the simplest, population model 70 directly stores in the computer each individual test subject's model 50 as separate a sample record in a database. The sample record may include the test subject's block 5 supplementary data and the test subject's individual model 50 (either as output from block 45 or after transforming the individual model data 50 to a common template). These sample records may be used subsequently to answer different database queries about the test subject population. For example, one may query and retrieve all sample records for female subjects between ages 40 and 50. In some embodiments, the sample records may be processed to determine statistical models 70 of the test subject population and/or of a subset of the test subject population. In some embodiments, the sample records may be used to determine reduced coordinate representations that may make it more efficient to retrieve and personalize models for individual target persons. By way of non-limiting example, one may utilize principal component analysis to represent the variations in model parameters (e.g. skin thickness) over the test subject population or a subset of the test subject population utilizing a small number of variables.

Figure 2:
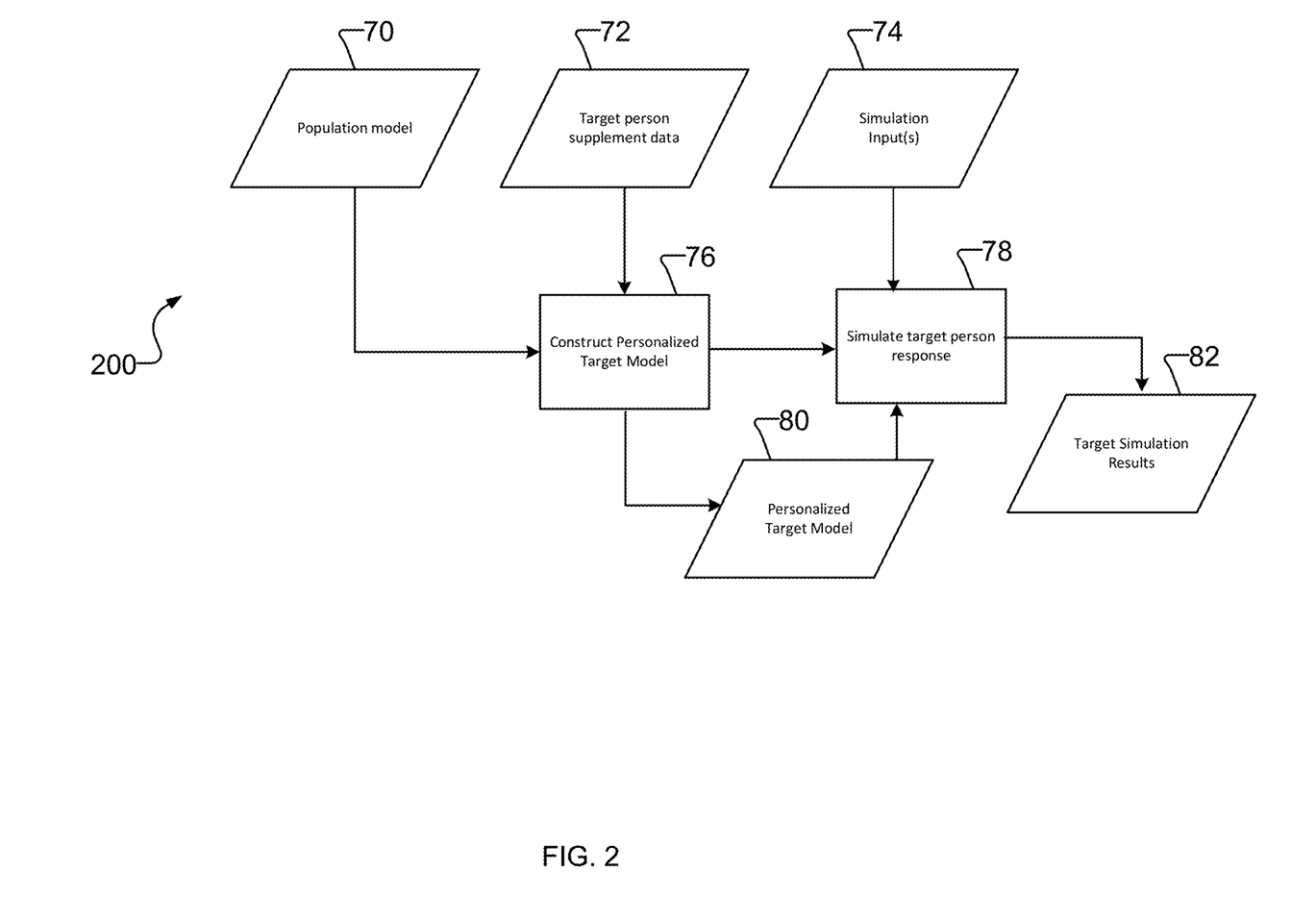
FIG. 2 is a block diagram of a method for simulating a response of a target person's body to contact using the FIG. 1 model according to one embodiment of the invention.

FIG. 2 is a block diagram of a method 200 for obtaining a simulation of (simulating) a response of a target person's body to contact according to one embodiment of the invention. The target person who is simulated using method 200 may be a test subject of method 100, but need not be.

Method 200 may receive, as input, population model 70. Population model 70 may be obtained as described in method 100 or by any other suitable method. In some embodiments, instead of population model 70, method 200 may receive the individual model 50 obtained by method 100 for the target person—i.e. the target person for method 200 is the only test subject of method 100. Method 200 may also receive, as input, supplemental data 72 of the target person. Such supplemental data 72 may include, for example, one or more items of data of the type included in the supplementary data collected in block 5 of method 100, such as, by way of non-limiting example, the target person's weight, height, body shape, one or more measurements of the target person's body, etc. The block 72 supplemental may include other data that may be correlated with the supplemental data obtained in block 5; for example, hair color data may be correlated with Fitzpatrick skin type. In some embodiments, the target person may be a fictional or virtual person and supplemental data 72 of the target person may comprise representations associated with: a statistical average (or percentile) person of a certain height or weight, an extrapolation of the population to a person who is heavier by two standard deviations than the average person, etc. Method 200 may also receive, as input, one or more simulation inputs 74 to be simulated. For example, such simulation inputs 74 may comprise a model of a garment or other object that interact with the body of the target person that may be simulated concurrently with the body. Simulation inputs 74 may, for example, comprise one or more static forces applied to the target person, one or more dynamic forces applied to the target person, one or more movements of the body of the target person, one or more forces applied by a garment to the target person, etc. Simulation inputs 74 may comprise time varying boundary conditions; by way of non-limiting example, the simulation input boundary conditions 74 may be Neumann boundary conditions, Dirichlet boundary conditions, mixed boundary conditions and/or the like.

To simulate a target person in block 78, a personalized target model 80 of the target person may be constructed in block 76 utilizing at least some of target person supplementary data 72 and/or population model 70.

At block 76, some of target person supplementary data 72 may be correlated with models 50 of test subjects, with portions of population model 70 and/or with supplementary data obtained for test subjects in block 5. As a non-limiting example a test subject's weight may be correlated with effective thickness and/or elasticity parameters of a suitable model for that test subject. Population model 70 may therefore be used to determine a mapping from a target person's supplementary data 72 to a prediction of the target person's model parameters (which may form part of a personalized target model 80). Such a mapping may employ any statistical method including, but not limited to, frequentist and Bayesian methods. A Bayesian method may permit the incorporation of prior beliefs and knowledge, such as the normative anatomy of all humans, into the block 76 process. The block 76 statistical method may utilize machine learning architectures such as deep neural networks to achieve the mapping.

In one embodiment, the mapping is learned as a composition of two mappings. The first mapping is constructed by performing Principal Component Analysis (PCA) to create a low-dimensional (e.g. much lower than the total number of dimensions) representation of the model parameters in the population model. Such a representation approximates a test subject's model parameters as a weighted linear combination of principal components. The first mapping maps PCA weights to model parameters. The second mapping is constructed between supplementary data in the population model and corresponding PCA weights, using feature analysis. Once the two mappings are learned, model parameters for a target person may be efficiently estimated by applying the second mapping to the target person supplementary data 72 to estimate target PCA weights and then applying the first mapping to the estimated target PCA weights to the PCA components to predict the target model parameters. The target model parameters thus constructed may be iteratively refined.

Method 200 then proceeds to block 78. At block 78 of method 200, personalized target model 80 and simulation inputs 74 are received as input to simulate body of the target person in response to the simulation inputs 74. Block 78 may output a target simulation (or animation) 82 which provides a simulation of a response of the target person's body to simulation inputs 74 based on personalized target model 80. Personalized target model 80 is not expressly required. In some embodiments, block 78 may involve the use of population model 70 and/or an individual test subject model 50 to generate simulation 82. Some non-limiting example embodiments of the types of simulation that may be performed in block 78 are described in Appendix B of the Provisional Application.

In some embodiments, the systems and methods described herein are not limited to humans and may be used for similar modeling and/or simulation of animals, such as, for example, pet animals, zoo animals, rescued wild animals, wild animals or the like.

Interpretation of Terms

Figure 3:
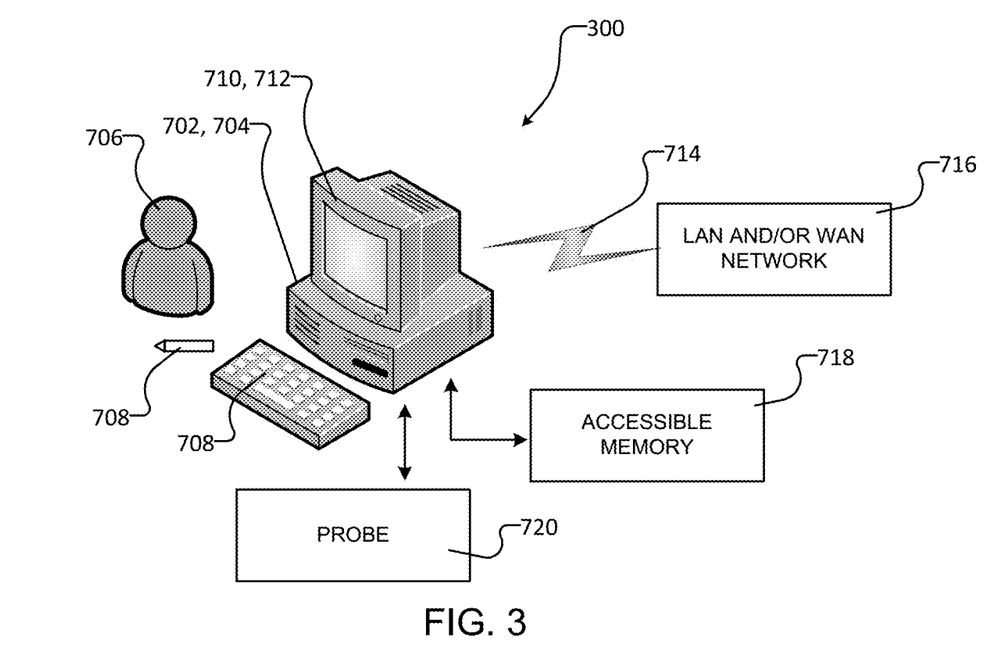
FIG. 3 schematically depicts one example of a computer system which may be used to practice aspects of the current invention according to a particular embodiment.

FIG. 3 is a schematic depiction of a particular embodiment of a computer system 300 which may be used to perform any of the methods described herein and the steps of any of the methods described herein according to a particular embodiment. Computer system 300 of the illustrated embodiment comprises one or more computers 702 which may comprise one or more processors 704 which may in turn execute suitable software (not expressly enumerated) accessible to processor(s) 704. When such software is executed by computer 702 (and in particular processor(s) 704), computer 702 and/or processor(s) 704 may perform any of the methods described herein and the steps of any of the methods described herein. In the illustrated embodiment, computer 702 provides a user interface 710 for interaction with a user 706. From a hardware perspective, user interface 710 comprises one or more input devices 708 (a stylus and a keyboard are shown in the illustrated embodiment) in by which user 706 can input information to computer 702 and one or more output devices 712 (a monitor is shown in the illustrated embodiment) by which information can be output to user 706. In general, input devices 708 and output devices 712 are not limited to those shown in the illustrated embodiment of FIG. 3. In general, input device 708 and output device 712 may comprise any suitable input and/or output devices suitable for interacting with computer 702—e.g. a stylus on a "touch-screen" tablet. User interface 710 may also be provided in part by software when such software is executed by computer 702 and/or its processor(s) 704. In the illustrated embodiment, computer 702 is also connected to access data (and/or to store data) on accessible memory device 718. In the illustrated embodiment, computer 702 is also connected by communication interface 714 to a LAN and/or WAN network 716, to enable accessing data from networked devices (not shown) and/or communication of data to networked devices.

Input (e.g. supplemental test subject data 5, measured data 20 (FIG. 1)) may be obtained by computer 702 via any of its input mechanisms, including, without limitation, by any input device 708, from accessible memory 718, from network 716 or by any other suitable input mechanism. The outputs (e.g. model of current test subject 50) may be output from computer 702 via any of its output mechanisms, including, without limitation, by any output device 712, to accessible memory 718, to network 716 or to any other suitable output mechanism. As discussed above, FIG. 3 is merely a schematic depiction of a particular embodiment of a computer-based system 300 suitable for implementing the methods described herein. Suitable systems are not limited to the particular type shown in the schematic depiction of FIG. 3 and suitable components (e.g. input and output devices) are not limited to those shown in the schematic depiction of FIG. 3.

While not expressly shown in FIG. 3, computer system 300 is also communicatively coupled with a probe 720 of the type described throughout this disclosure for measuring characteristics of subjects.

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof; elements which are integrally formed may be considered to be connected or coupled;
- language indicative of examples (such as, for example, "such as", "for example" and "e.g.") should be interpreted to mean "by way of non-limiting example". Any such examples should not be interpreted as being necessary;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list; and
- the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a computer system for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Software and other modules may reside on servers, workstations, personal computers, tablet computers, image data encoders, image data decoders, PDAs, color-grading tools, video projectors, audio-visual receivers, displays (such as televisions), digital cinema projectors, media players, and other devices suitable for the purposes described herein. Those skilled in the relevant art will appreciate that aspects of the system can be practised with other communications, data processing, or computer system configurations, including: Internet appliances, hand-held devices (including personal digital assistants (PDAs)), wearable computers, all manner of cellular or mobile phones, multi-processor systems, microprocessor-based or programmable consumer electronics (e.g., video projectors, audio-visual receivers, displays, such as televisions, and the like), set-top boxes, color-grading tools, network PCs, mini-computers, mainframe computers, and the like.

Embodiments of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g. EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components which are not structurally equivalent to the disclosed structure which performs the function in the illustrated exemplary embodiments of the invention.

Where a record, field, entry, and/or other element of a database is referred to above, unless otherwise indicated, such reference should be interpreted as including a plurality of records, fields, entries, and/or other elements, as appropriate. Such reference should also be interpreted as including a portion of one or more records, fields, entries, and/or other elements, as appropriate. For example, a plurality of "physical" records in a database (i.e. records encoded in the database's structure) may be regarded as one "logical" record for the purpose of the description above and the claims below, even if the plurality of physical records includes information which is excluded from the logical record.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

The invention claimed is:

1. A method for simulating a response of a target person to one or more simulation inputs, the method comprising:
   contacting a first location of a body of a first test subject with a probe tip mechanically connected to a force sensor;
   measuring a first force applied to the probe tip by the first location of the body of the first test subject with the force sensor;
   obtaining a first relative movement, the first relative movement comprising a first movement of the probe tip relative to the first location of the body of the first test subject;
   contacting a second location of a body of a second test subject with the probe tip;
   measuring a second force applied by the probe tip to the second location of the body of the second test subject with the force sensor;
   obtaining a second relative movement, the second relative movement comprising a first movement of the probe tip relative to the second location of the body of the second test subject;
   determining one or more model parameters of a target model associated with at least a portion of a body of a target person based on the first force and the first relative movement and the second force and the second relative movement;
   obtaining a simulation input for application to the target model; and
   over a series of discrete time steps, simulating a response of the at least a portion of the body of the target person in response to the simulation input using the target model, wherein simulating the response comprises using the target model to generate, for each discrete time step, at least one of: a simulated shape of a surface of the portion of the body of the target person; and simulated stresses and strains internal to the portion of the body of the target person.

2. A method according to claim 1 wherein determining one or more model parameters of the target model comprises:
   creating a first test subject model comprising one or more model parameters associated with the first location of the body of the first test subject based on the first force and the first relative movement;
   creating a second test subject model comprising one or more model parameters associated with the second location of the body of the second test subject based on the second force and the second relative movement; and
   basing one or more model parameters of the target model on a weighted combination of the first test subject model and the second test subject model.

3. A method according to claim 2 comprising:
   for each of the first subject and the second subject, obtaining supplementary test subject data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the first or second test subject;

for the target person, obtaining supplementary target person data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the target person; and wherein the weighted combination of the first test subject model and the second test subject model is based at least in part on a comparison of the target person supplementary data with the first test subject supplementary data and a comparison of the target person supplementary data with the second test subject supplementary data.

4. A method according to claim 1 wherein determining one or more model parameters of the target model comprises:

constructing a population model, the population model based on: a first test subject model comprising one or more model parameters associated with the first location of the body of the first test subject based on the first force and the first relative movement and a second test subject model comprising one or more model parameters associated with the second location of the body of the second test subject based on the second force and the second relative movement; and constructing the target model based on the population model.

5. A method according to claim 4 wherein constructing the target model based on the population model comprises constructing the target model based on a weighted combination of the one or more model parameters associated with the first location of the body of the first test subject and the one or more second model parameters associated with the second location of the body of the second test subject.

6. A method according to claim 5 comprising:

for each of the first subject and the second subject, obtaining supplementary test subject data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the first or second test subject;

for the target person, obtaining supplementary target person data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the target person; and wherein the weighted combination of the one or more model parameters associated with the first location of the body of the first test subject and the one or more second model parameters associated with the second location of the body of the second test subject is based at least in part on a comparison of the target person supplementary data with the first test subject supplementary data and a comparison of the target person supplementary data with the second test subject supplementary data.

7. A method according to claim 4 wherein constructing the target model based on the population model comprises generating the target model based on a statistical abstraction of the population model.

8. A method according to claim 7 comprising:

for each of the first subject and the second subject, obtaining supplementary test subject data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the first or second test subject;

for the target person, obtaining supplementary target person data comprising one or more of: body shape, 3D body shape scans, 3D body shape scans with calibration garments, body weight, body height, locations of anatomical landmarks, anthropometric measurements such as waist and bust size, biological sex, age, body mass index (BMI), ethnicity, Fitzpatrick skin type, clothing size, exercise preferences and/or the like, of the target person; and wherein the statistical abstraction of the population model is based at least in part on a comparison of the target person supplementary data with the first test subject supplementary data and a comparison of the target person supplementary data with the second test subject supplementary data.

9. A method according to 1 wherein determining the one or more model parameters associated with the first location of the target person comprises:

mapping the first location of the first test subject to a first location on a target person; and mapping the second location of the second test subject to the first location on the target person.

10. A method according to claim 9 wherein mapping the first location of the first test subject to the first location on the target person is based at least in part on supplementary test subject data comprising one or more of: body shape, a three-dimensional body scan, body weight, body height, body mass index, locations of anatomical landmarks, anthropometric measurements, ethnicity, Fitzpatrick skin type, clothing size, and exercise preferences.

11. A method according to claim 9 wherein mapping the second location of the second test subject to the first location on the target person is based at least in part on supplementary test subject data comprising one or more of: body shape, a three-dimensional body scan, body weight, body height, body mass index, locations of anatomical landmarks, anthropometric measurements, ethnicity, Fitzpatrick skin type, clothing size, and exercise preferences.

12. A method according to claim 1 wherein mapping the first location of the first test subject to the first location on the target person comprises mapping an anatomical landmark of the first test subject to an anatomical landmark of the target person.

13. A method according to claim 1 wherein mapping the second location of the second test subject to the first location on the target person comprises mapping an anatomical landmark of the second test subject to an anatomical landmark of the target person.

14. A method according to claim 1 wherein simulating the response of the at least a portion of the body of the target person comprises simulating an interaction of the target model with a clothing model.

15. A method according to claim 14 wherein simulating the response comprises evaluating, preferably quantifying, a fit of the garment on the body of the target person.

16. A method according to claim 1 comprising:
accommodating for the measured first movement of the test subject within the measured first movement of the probe tip to obtain a first relative movement;
accommodating for the measured second movement of the test subject within the measured second movement of the probe tip to obtain a second relative movement; and
wherein determining one or more model parameters associated with the first and second locations of the body of the first test subject is based on the first and second forces and the corresponding first and second relative movements.

17. A method according to claim 1 wherein the one or more model parameters comprise one or more of: elasticity, mass density, skin friction, reference body shape, and effective skin thickness of the first test subject.

18. A method according to claim 1 wherein the one or more model parameters comprise one or more sliding thick skin model parameters.

19. A system for simulating a response of a target person to one or more simulation inputs, the system comprising one or more computing devices configured to:
obtain a first relative movement, the first relative movement obtained by:
contacting a first location of a body of a first test subject with a probe tip mechanically connected to a force sensor; and
measuring a first force applied to the probe tip by the first location of the body of the first test subject with the force sensor;
the first relative movement comprising a first movement of the probe tip relative to the first location of the body of the first test subject;
obtain a second relative movement, the second relative movement obtained by:
contacting a second location of a body of a second test subject with the probe tip;
measuring a second force applied by the probe tip to the second location of the body of the second test subject with the force sensor;
the second relative movement comprising a first movement of the probe tip relative to the second location of the body of the second test subject;
determine one or more model parameters of a target model associated with at least a portion of a body of a target person based on the first force and the first relative movement and the second force and the second relative movement;
obtain a simulation input for application to the target model; and
over a series of discrete time steps, simulate a response of the at least a portion of the body of the target person in response to the simulation input using the target model, wherein simulating the response comprises using the target model to generate, for each discrete time step, at least one of: a simulated shape of a surface of the portion of the body of the target person; and simulated stresses and strains internal to the portion of the body of the target person.

* * * * *